United States Patent [19]
Low et al.

[11] Patent Number: 5,837,231
[45] Date of Patent: Nov. 17, 1998

[54] GM-CSF ADMINISTRATION FOR THE TREATMENT AND PREVENTION OF RECURRENCE OF BRAIN TUMORS

[75] Inventors: Walter C. Low, Shorewood; Margaret A. Wallenfriedman, Edina, both of Minn.

[73] Assignee: Regents of the University of Minnesota, Minneapolis, Minn.

[21] Appl. No.: 671,251

[22] Filed: Jun. 27, 1996

[51] Int. Cl.⁶ .......................... A61K 38/19; A61K 35/12; A61K 38/00
[52] U.S. Cl. .................... 424/85.1; 424/277.1; 424/93.7; 514/2
[58] Field of Search .............. 424/85.1, 227.1, 424/93.7; 514/2

[56] References Cited

U.S. PATENT DOCUMENTS

| | | | |
|---|---|---|---|
| 5,165,922 | 11/1992 | Hellstrom et al. | 424/85.8 |
| 5,208,022 | 5/1993 | Eggers | 424/88 |

FOREIGN PATENT DOCUMENTS

| | | |
|---|---|---|
| WO 93/06867 | 4/1993 | WIPO . |
| WO 94/16716 | 8/1994 | WIPO . |

OTHER PUBLICATIONS

Pardoll, DM. 1995, Annu. Rev. Immunol. 13:399–415.
Wakinoto, H et al. 1996. Cancer Res. 56:1828–33.
Sampson, JH. et al. 1996. Proceed. Amer. Assoc. Cancer Res. 37:339.
Ellem, K. AO. 1997. Cancer Immunol. Immunother. 44:10–20.
Coleman, et al. *The Journal of Immunology*, 143:4134–4140(Dec. 15, 1989).
Colombo, et al. *J. Exp. Med.*, 173:889–897(Apr. 1991).
Falk, et al. *Journal of Leukocyte Biology*, 43:471–476(1988).
Grabstein, et al. *Science*, 232:506–508 (Apr. 25, 1986).
Heufler, et al. *J. Exp. Med.*, 167:700–705(Feb. 1988).
Markowicz, et al. *J. Clin. Invest.*, 85:955–961 (Mar. 1990).
Witmer–Pack, et al. *J. Exp. Med.*, 166:1484–1498 (Nov. 1987).
Abe, et al., *Cancer Gene* Therapy, 1:312 (1994).
Anderson, *Science*, 256:808–813 (May 8, 1992).
Asher, et al., *The Journal of Immunology*, 146:3227–3234 (May 1, 1991).
Blankenstein, et al., *J. Exp. Med.*, 17:1047–1052 (May 1991).
Dranoff, et al., *Proc. Natl. Acad. Sci. USA*, 90:3539–3543 (Apr. 1993).
Elliot, et al., *J. Clin. Invest.*, 86:80–86 Jul. 1990).
Elliott, et al., *J. Neurosurgery*, 67:231–236 (Aug. 1987).
Fearon, et al., *Cell*, 60:397–403 (Feb. 9, 1990).
Fontana, et al., *J. Immunol.*, 132:1837–1844 (Apr. 1984).
Frei, *Neuropathology and Applied Neurobiology*, 20:206–208 (1994).
Gansbacher, et al., *Cancer Research*, 50:7820–7825 (Dec. 15, 1990).

Gansbacher, et al., *J. Exp. Med.*, 172:1217–1224 (Oct. 1990).
Hock, et al., *J. Exp. Med.*, 174:1291–1298 (Dec. 1991).
Holladay, et al., *J. Neurosurgery*, 80:90–96 (Jan. 1994).
Inaba, et al., *J. Exp. Med.*, 176:1693–1702 (Dec. 1992).
Kämpgen, et al., *J. Exp. Med.*, 179:1767–1776 (Jun. 1994).
King, et al., *Immunology Today*, 11:206–211 (1990).
Kurpad, et al., *Seminars in Oncology*, 21:149–161 (Apr. 1994).
Lampson, et al., *J. Immunol.*, 136:4054–4062 (Jun. 1, 1986).
Lee, et al., *J. Clin. Oncol.*, 7:7–20 (Jan. 1989).
Levin, et al., in *Cancer Principles and Practice of Oncology*, V. T. DeVita, et al., eds., J. B. Lippincott Co., Philadelphia, PA, 2:1679–1737 (1993).
Mahaley, et al., *J. Neurosurgery*, 71:826–836 (Dec. 1989).
Morioka, et al., *Neurosurgery*, 30:891–896 (1992).
Morioka, et al., *Acta Neuropathol.*, 83:590–597 (1992).
Myers, et al., *J. Neurosurg.*, 76:986–990 (Jun. 1992).
Paglia, et al., *J. Exp. Med.*, 178:1893–1901 (Dec. 1993).
Porgador, et al., *Cancer Research*, 52:3679–3686 (Jul. 1, 1992).
Reid, et al., *The Journal of Immunology*, 149:2681–2688 (Oct. 15, 1992).
Restifo, et al., *The Journal of Exp. Med.*, 175:1423–1431 (Jun. 1992).
Rosenberg, et al., *N. Engl. J. Med.*, 316:889–897 (Apr. 9, 1987).
Roszman, et al., *Immunology Today*, 12:370–374 (1991).
Sanda, et al., *The Journal of Urology*, 151:622–628 (Mar. 1994).
Schwyzer, et al., *J. Immunol.*, 134:1003–1009 (Feb. 1985).
Steinman, *Annu. Rev. Immunol.*, 9:271–296 (1991).
Tada, et al., *Journal of Neuro–Oncology*, 17:261–271 (1993).
Tzeng, et al., *Cancer Res.*, 50:4338–4343 (Jul. 15, 1990).
Urbani, et al., *Journal of Interferon and Cytokine Research*, 15:421–429 (1995).
Watanabe, et al., *Proc. Natl. Acad. Sci. USA*, 86:9456–9460 (Dec. 1989).
Wen, et al., *J. Neuroimmunol.*, 36:57–68 (1992).
Osband, M.E. 1990 Immunology Today 11:193–195.
Disis, M.L et al. 1995. 9ᵗʰ Duterudtl. Congress Immunology, 582.
Stevenson, F.K. et al. 1995 Immunol. Review, 145:211–228.

*Primary Examiner*—Lila Feisee
*Assistant Examiner*—Geetha P. Bansal
*Attorney, Agent, or Firm*—Merchant, Gould, Smith, Edell, Welter & Schmidt, P.A.

[57] ABSTRACT

A method for inhibiting the growth of brain tumors comprising peripheral administration of GM-CSF in combination with brain tumor antigen.

11 Claims, 4 Drawing Sheets

GM-CSF ADMINISTRATION FOR THE TREATMENT AND PREVENTION OF RECURRENCE OF BRAIN TUMORS

FIELD OF THE INVENTION

This invention relates to a therapeutic method effective for inhibiting the growth of brain tumors and preventing their reoccurrence. Specifically, the invention demonstrates that the peripheral administration of GM-CSF in combination with brain tumor antigens effectively inhibits growth of tumor cells in the brain. After such treatment, animals are resistant to further tumor challenges.

BACKGROUND OF THE INVENTION

Brain tumors are a leading cause of death from neurological disease. It has been estimated that approximately 11,000 people in the United States alone die each year from primary tumors of the central nervous system. The most malignant form of primary intracranial tumors is glioblastoma multiforme. The mean survival time for patients with this type of tumor in the absence of any therapy is 14 weeks with a 1-year survival rate of 3%. With surgery, radiation therapy, and chemotherapy, the survival times are not dramatically prolonged. A key problem in dealing with glioblastoma is the inability of the immune system to recognize and destroy these tumor cells.

Glial derived brain tumors represent a population of tumors with the capacity to evade and ultimately inhibit the body's mechanism for tumor defense. Clinical observations of patients with glioblastoma suggest that both cell mediated and humoral immunity are suppressed. These patients display cutaneous anergy, decreased numbers of T-cells and diminished responses to mitogens and antigens. Their peripheral blood lymphocytes fail to produce $\gamma$-interferon (IFN-$\gamma$), granulocyte/macrophage colony stimulating factor (GM-CSF) and tumor necrosis factor-$\alpha$ (TNF-$\alpha$) upon stimulation in vitro. When stimulated, T-cells from glioma patients express abnormally low levels of p55, the subunit which confers high affinity to the interleukin-2 (IL-2) receptor.

The mechanisms of glioma-induced immuno-suppression are not clear. Gliomas have a low level of MHC Class I antigen expression and minimal tumor infiltration by lymphocytes. Sera from glioma patients suppresses normal lymphocyte function, as does culture supernatant from surgically removed glioblastomas. The "glioblastoma derived T-cell suppressor factor" (G-TSF) was isolated from such glioma supernatant.

GM-CSF inhibits the activity of normal T-cells and is homologous to transforming growth factor $\beta 2$ (TGF$\beta 2$). This factor appears to be responsible for the decreased levels of p55 seen in T-cells from glioma patients.

Current treatment of brain tumors, glioblastoma, medulloblastoma, and others, by surgical excision, radiation or chemical therapy, have not changed mean survival over the last decade. Given glioma's ability to suppress host defenses, it is not surprising that tumor cells which survive treatment will regrow. Therefore, therapeutic methods to enhance the immune system's detection and control of tumors, and especially of gliomas are greatly needed.

In vivo mmunological defense against brain tumors, e.g., glioma is limited to MHC-restricted, antigen-specific cytotoxic T-lymphocytes (CTL). There is no evidence for antibody production against glioma tissue associated antigens, and glioma cells are resistant to natural killer (NK) cells. In the normal immune system, MHC-restricted cellular cytotoxicity begins with macrophages such as microglia in the brain, and Langerhan's cells in the epidermis. These sentinel cells phagocytose tumors and present digested peptide antigens on the macrophage's MHC II molecules. Stimulation by cytokines causes Langerhans' cells to migrate and differentiate into peripheral dendritic cells, thought to be the major source of immunological epitopes for T-cell activation. These antigen presenting cells (APC) then activate CD4$^+$ helper T-cells (Th-1) in the presence of macrophage-produced IL-12. Th-1 cells' T-cell receptor (TCR), to which CD4 is coupled, binds to a specific MHC II restricted antigen on the APC. Once activated, Th-1 cells release IL-2 and IFN-$\gamma$ to activate antigen-specific cytotoxic CD8$^+$ T-cells and macrophages. The activated macrophages release TNF-$\alpha$ to kill tumor cells. The activated CTL have CD8-coupled TCR's which interact with MHC I restricted antigens on tumor surfaces. This antigen-specific recognition actuates CTL to lyse and destroy the tumor cell.

The events leading to CTL activation may be divided into tasks attributed to one of two functional groups: antigen presenting "sensor" cells and lymphocytic "effector" cells. Immunological therapies to date have primarily focused on augmenting the lymphocytic "effector" cells. Lymphocytes such as tumor-infiltrated lymphocytes, (TILs) or peripheral lymphokine-activated killer cells (LAK cells) have been harvested from patients, expanded or stimulated with lymphokines ex vivo, and re-introduced back into the patient. The efficacy of this approach is dependent upon concurrent systemic infusion of IL-2. This immunotherapy has met with some success in the treatment of melanoma and renal cell carcinoma, however, it has not been successful in treating brain tumors, especially glioma.

Brain tumors, e.g., gliomas, have very few tumor-infiltrating lymphocytes and despite the effectiveness of LAK cells in vitro, they do not reduce gliomas in vivo. Additionally, there are serious side effects of high concentrations of systemic IL-2, including vascular leaks resulting in cerebral edema, making this therapy particularly undesirable.

GM-CSF has long been recognized as a proliferative factor for macrophages and granulocytes. However, its immunological potential has only recently been appreciated. Endogenous tumoricidal activity has been stimulated in animals immunized with tumor cell transfected with cytokines, including IL-2 into fibrosarcoma and colon carcinoma; TNF $\alpha$ into plasmacytoma and sarcoma; IL-7 into plasmacytoma; IFN $\gamma$ into neuroblastoma, fibrosarcoma, and sarcoma; IL-6 into lung carcinoma, and GM-CSF into colon carcinoma, melanoma, and prostate carcinoma. When compared with other cytokines, GM-CSF alone (or in combination with IL-2), has been found to be the most potent stimulator of systemic antitumor immunity. Moreover, tumors transfected with the gene encoding GM-CSF evoked a long lasting immune response that was generalizable to the non-transfected cells.

The majority of work to date studying on the tumoricidal potential of GM-CSF has been done by viral transfections of tumor cell lines with recombinant DNA encoding GM-CSF. While these techniques are easily performed in the laboratory using clonal cell populations, the many practical limitations of applying these techniques clinically in the brain are clear. First, the consequences of inserting viral DNA into human brain tumors, e.g., gliomas is unknown. An estimated 23 years of retroviral mediated gene transfer has been performed in humans without known side effects, although some of the viral vectors being used for gene therapy have long-term potential for causing cancer. Side effects have been described in 3 monkeys at the NIH, who developed malignant T cell lymphoma after bone marrow transplant and gene transfer with a helper virus-contaminated retrovirus. Second, a therapy is needed that can be quickly and easily administered to a large number of patients. The development of custom transfections of each patient's glioma cell line with a viral vector containing GM-CSF would be labor intensive and economically impractical.

Further, in contrast to other types of cancer, the treatment of brain tumors, e.g., gliomas, presents extraordinary limitations. Peripheral delivery of immunogenic agents and enhancers must activate an immune response capable of exerting its effects across the blood-brain barrier. Agents delivered to peripheral sites must produce a therapeutic effect that is effective against tumors in the brain. Such effects are not predictable from successful in vitro studies or from studies with peripheral tumors.

It would be highly desirable to develop a therapeutic method and composition for the treatment of brain tumors and particularly of gliomas, that could employ peripheral delivery techniques and could adequately and comprehensively stimulate the immune system to halt growth and inhibit recurrence of tumors in the brain.

SUMMARY OF THE INVENTION

It has now been found that the peripheral administration of GM-CSF in combination with irradiated brain tumor cells successfully stimulates the immune system. The effect crosses the blood-brain barrier, prohibits the continued growth of tumors in the brain, and protects the treated animal from further tumor challenges. GM-CSF, in the absence of additional cytokines such as IL-2, when co-administered peripherally with brain tumor antigens (e.g., apoptotic irradiated tumor cells), adequately stimulates a long lasting immune response that prevents tumor growth in the brain.

DETAILED DESCRIPTION OF THE PREFERRED EMBODIMENTS

GM-CSF

Figure 1:
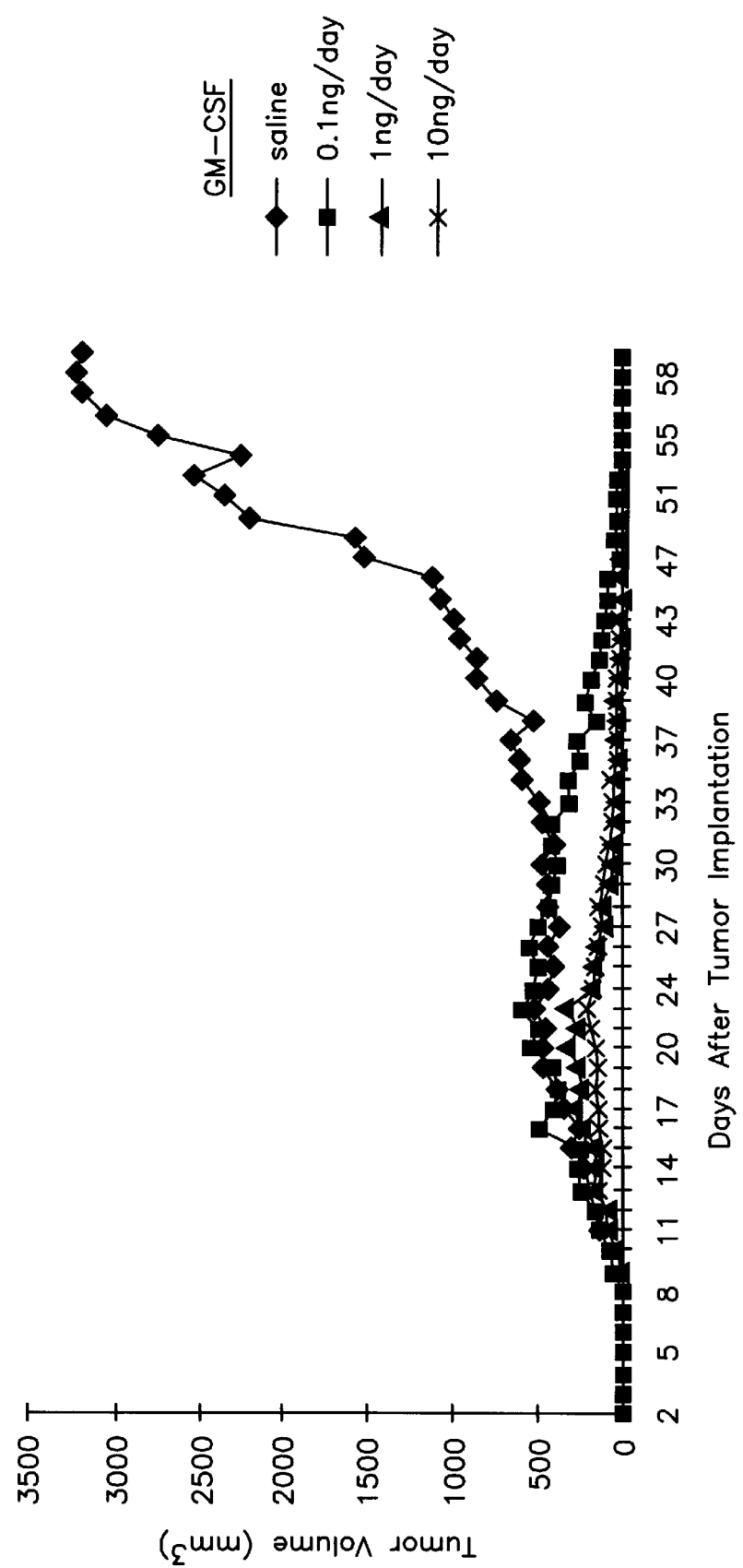
FIG. 1 is a graph showing the effects of peripheral co-administration of GM-CSF and inactivated 9L cells on the growth of 9L glioblastoma tumors in the flank of host animals.

GM-CSF is a small, 144 amino acid protein having multiple sites of glycosylation, an N-terminal signal sequence, and a C-terminal receptor binding domain (Rasko and Gough In: *The Cytokine Handbook*, A. Thomson, et al, Academic Press, New York (1994) pages 349–369). Its three-dimensional structure is similar to that of the interleukins, although the amino acid sequences are not similar.

Human, recombinant GM-CSF is commercially available from Immunex (Seattle, Wash.). GM-CSF is administered, preferably by continuous infusion, to peripheral, subcutaneous tissues, in an aqueous medium, e.g. PBS. Human clinical studies using GM-CSF to stimulate granulocytes and macrophages after chemotherapy have demonstrated patient tolerance of up to 2100 µg/day by intravenous infusion and up to 700 µg/day by subcutaneous injection without evidence of deleterious side effects. A useful dose range in murine studies was 0.1 ng–10 ng/day; thus, the expected useful human clinical range of GM-CSF administered is about 200 ng–1000 µg/day, and preferably about 1 µg–500 µg/day. Most preferably, the expected human clinical dosage rate is in the range of about 5 µg–40 µg/day.

GM-CSF is administered by methods known for administration of a peptide therapeutic agent. Preferably, administration is by injection, and most preferably by continuous infusion in an aqueous carrier such as phosphate buffered saline (PBS).

TUMOR ANTIGEN

The phrase "tumor antigen" is defined in this application, includes inactivated (e.g. irradiated), whole and lysed tumor cells, and antigenic portions thereof (e.g., membranes, peptides, etc.). The tumor antigen is derived from the specific patient's tumor, e.g. from biopsy tissue or from explants of a removed tumor, or from cell culture of the patient's brain tumor cells. The patient's brain tumor cells are obtained by standard biopsy methods. Cells from excised tumor tissue can be directly used, or alternatively, cells of the excised tumor can be cultured and expanded under standard culture conditions to produce increased numbers of cells for use as tumor antigen.

Tumor cells are inactivated by methods known in the field, the most common method being irradiation as described in the examples below. Other known inactivation methods include oxygen deprivation, use of plant and animal toxins, and chemotherapeutic agents. Lysed tumor cells may also be used as the tumor antigen, as well as cell membranes and specific tumor cell protein antigens.

For administration, the tumor antigen is suspended in an aqueous medium, e.g., PBS. The amount of tumor antigen administered is that sufficient to induce an immune response. In rat studies, administration of five million irradiated tumor cells in 300 µl PBS was efficient in preventing tumor growth, when co-administered with GM-CSF. Thus, the expected useful human dose of irradiated tumor cells for subcutaneous injection is in the range of about one million to about 50 million cells, preferably about five million to 30 million cells. Administration of other types of tumor antigens, e.g. cell membrane or purified tumor cell antigens are administered to deliver a like amount of antigen.

METHODS OF ADMINISTRATION

In the method of the invention, administration of both GM-CSF and brain tumor antigen for the treatment of brain tumors is to a peripheral site, preferably by subcutaneous injection. Preferred peripheral sites for administration include the upper arm, thigh, and trunk areas of the body. It is preferred that tumor antigen is administered to the same peripheral location as GM-CSF administration.

While it is contemplated that delivery of GM-CSF and tumor antigen may be simultaneous and in a single composition, the preferred route of administration is continuous infusion of the GM-CSF (e.g., for at least about 20–30 days or more, depending upon immune response)

with injection of the tumor antigen, e.g., at weekly intervals, beginning on the first day of GM-CSF administration. Continuous administration of GM-CSF appears to be more effective than bolus injections.

Administration of GM-CSF is preferably continuous over the treatment period. Timing of tumor antigen administration is as needed to induce immune reactivity, and can be monitored by assessing change in tumor size (e.g., by MRI), immune response (e.g., by delayed type hypersensitivity skin test), and by measuring IFN-gamma secretion by the patient's TH-1 cells in response to tumor antigen.

Preferably administration of the two active agents is "essentially simultaneous", meaning the GM-CSF and tumor antigen are administered to the same peripheral location at the same treatment time to induce their synergistic effect. Most preferaly, tumor antigen is administered to the same subcutaneous site where GM-CSF is being infused. Continuous, subcutaneous infusion of GM-CSF is generally accomplished by attaching a pump filled with GM-CSF to plastic tubing. Both the tubing and pump are preferably placed beneath the skin. The pump is refilled by injecting a syringe filled with GM-CSF through the skin and into the pump reservoir. Tumor antigen is preferably injected by filling a syringe with inactivated antigen, e.g., irradiated tumor cells, and injecting near the tip of the plastic tubing where GM-CSF is being pumped out beneath the skin.

Treatment with both GM-CSF and tumor antigen is preferably continued until immune response is detected and/or tumor ablation is achieved.

PATIENT POPULATIONS

Patients suffering from all types of primary brain tumors are treated by the method of the invention. The successful peripheral co-administration of GM-CSF and tumor antigen for the treatment of brain tumors is surprising, given the distant location of the tumors and the potential impedance of the blood-brain barrier.

The method of treating with GM-CSF in combination with tumor antigen is particularly useful in preventing tumor reoccurrence, for example, after tumor reduction techniques, such as surgical debulking removal, irradiation, and/or chemotherapy. Co-administration of GM-CSF and tumor antigen may effectively inhibits regrowth of tumor, e.g. from residual tumor cells.

The invention is further defined by reference to the following examples which are exemplary in nature and not intended to limit the scope of the invention.

EXAMPLE 1

GM-CSF Dose-Response Effects

The effects of the localized administration of GM-CSF at different concentrations and in the presence of irradiated 9L cells on the growth of 9L rodent glioblastoma tumors implanted into the flank of immunocompetent rats was examined. Peripheral tumors were initiated by injection of 10 million non-irradiated 9L tumor cells (obtained from Dr. Patrick Wen, Harvard University) into the left flank of Fisher 344 rats (150–200 g, female, Harlan).

At the time of tumor initiation, murine GM-CSF (R&D Systems) (0, 0.1, 1.0, or 10 ng/day; 1 million units/20 micrograms) was infused subcutaneously into the animal's right flank using surgically implanted osmotic minipumps (Alzet, model 2004). These minipumps were set to release GM-CSF at a rate of 0.25 µl per hour over a period of 28 days. The method of initiating tumors at the start of treatment mimics the surgical condition, where a tumor has been debulked, but some cells remain, post operatively, to induce reoccurrence of tumors.

At the site of continuous GM-CSF infusion, near the tip of the plastic tubing, $5 \times 10^6$ irradiated 9L glioblastoma cells (in 300 µl PBS) were injected subcutaneously on days 0, 3, 7, 14 and 21 after tumor implantation. The 9L cells are syngeneic to the Fischer 344 rat strain rats, and were injected to stimulate an immune response. Prior to injection, these cells were irradiated with 6000 rads of $^{137}$Cs. At days 3, 7, 14, and 21 after tumor implantation, animals received additional inoculations of irradiated 9L cells into the site of GM-CSF infusion. GM-CSF infusion was halted after 28 days.

Tumor growth was measured daily for a period of 58 days after implantation, using calipers. Tumor volume was calculated according to the equation:

$$(L \times W^2)/2,$$

where L=length (mm) and W=width (mm). Each tumor was measured daily by an observer who was blinded to the treatment groups.

The effects of co-administered GM-CSF and irradiated 9L cells on 9L glioblastoma tumor growth in the flank of host animals are shown in FIG. 1. Tumors became measurable by 11 days after implantation for animals in all groups. Tumors continued to grow for a short time period, but then began to regress for all treated animals with GM-CSF and tumor antigen. In contrast, animals treated with saline infusions displayed progressive increases in tumor size and achieved a mean tumor volume greater than 30,000 mm$^3$ at the end of 58 days.

Figure 2:
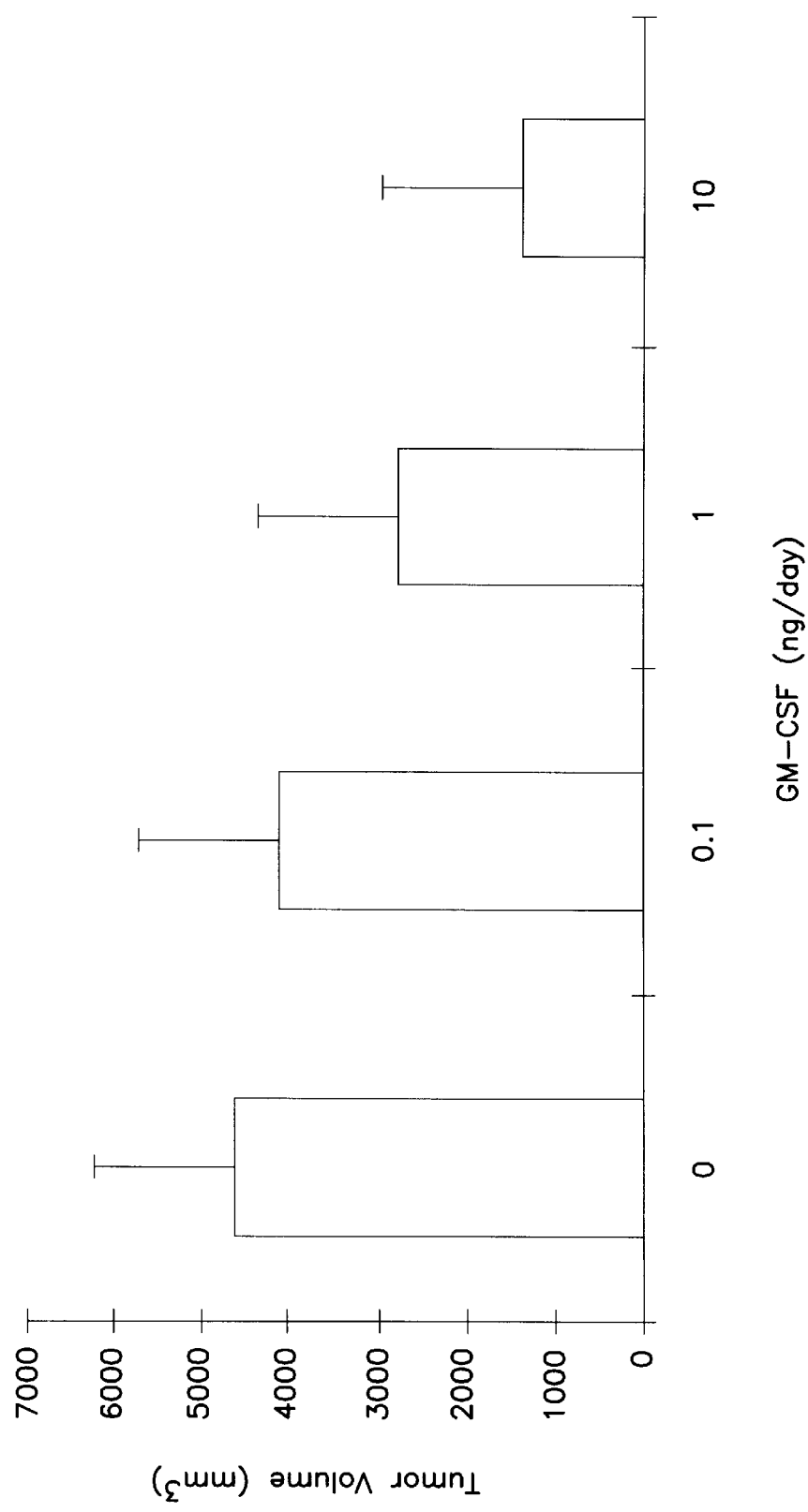
FIG. 2 is a graph showing a dose response effect of GM-CSF co-administered with tumor antigen on the growth of brain tumors in the flank of host animals.

Tumor growth rates from days 11 to 20 were dependent on GM-CSF concentration. At 20 days after implantation, animals treated with 10 ng/day of GM-CSF and tumor antigen, exhibited the slowest growing tumors followed by animals given 1 and 0.1 ng/day (FIG. 2).

EXAMPLE 2

GM-CSF and Irradiated Tumor Cells Effectively Prohibit Tumor Growth

Since the experiments of Example 1 showed the most effective GM-CSF dose for 9L tumor regression was 10 ng/day, this concentration was then used to determine whether the infusion of GM-CSF alone would be sufficient to stimulate an immune response, as compared with the co-administration of GM-CSF and irradiated tumor cells. In this experiment, intraflank 9L tumors were established as described for Example 1.

Treated animals received either (1) infusions of GM-CSF (10 ng/day), (2) infusions of GM-CSF plus irradiated tumor cells (five million cells in PBS), (3) infusions of saline plus irradiated tumor cells, or (4) no treatment. GM-CSF delivery and irradiated cell preparation and delivery was performed as described above for Example 1. Animals receiving irradiated tumor cells were inoculated during the day of tumor implantation (day 0) and at 3, 7, 14, and 21 days after the implantation of the non-irradiated tumor cells. GM-CSF delivery began on the day of tumor cell injection and followed continuously throughout the treatment protocol for 28 days.

Figure 3:
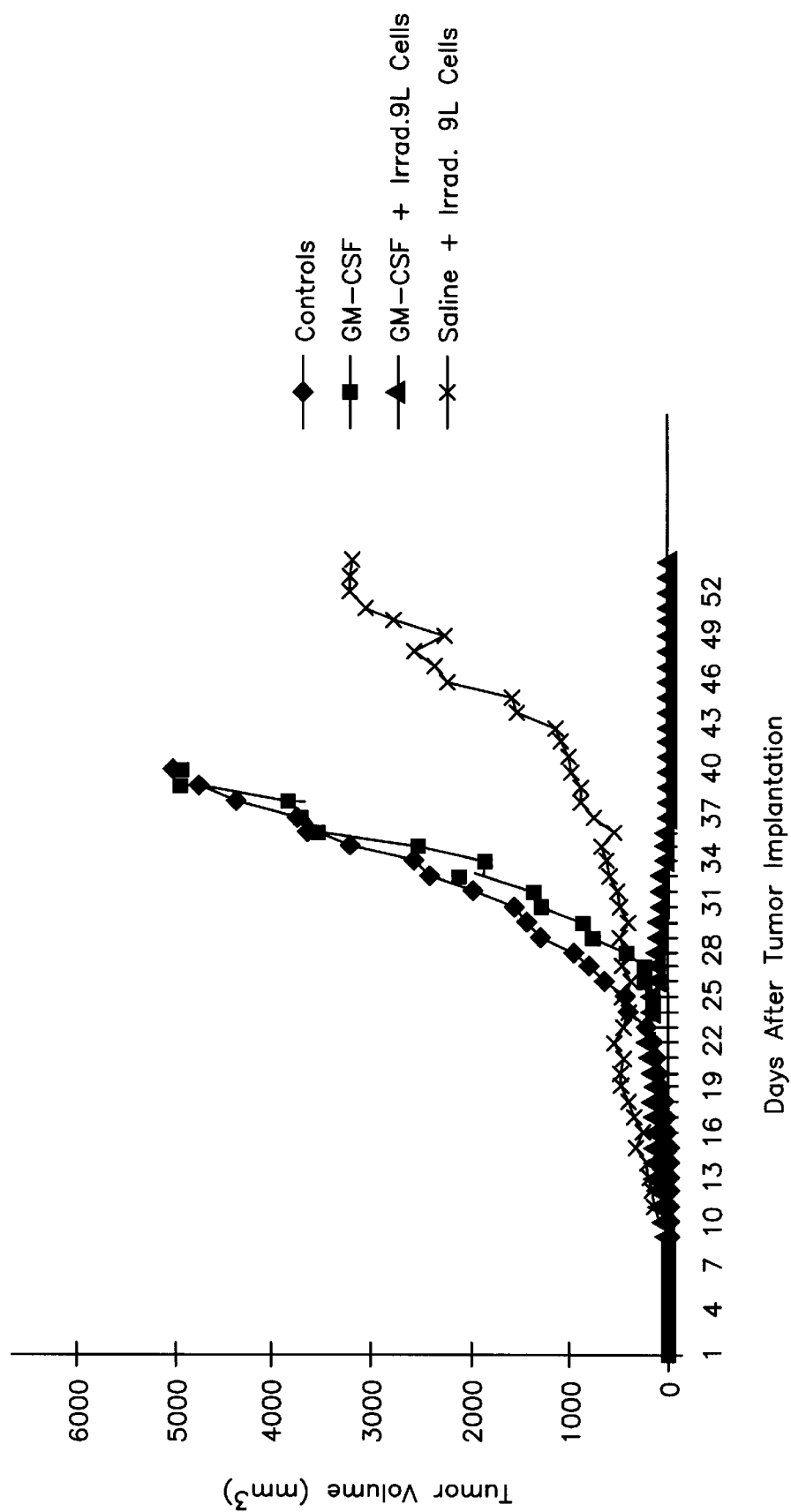
FIG. 3 is a graph comparing the effect of GM-CSF or tumor antigen administered alone with co-administration of both agents.

Non-treated animals exhibited a rapid rate of tumor growth (FIG. 3). The mean tumor volume in this group was greater than 50,000 mm$^3$ by 37 days after tumor implantation. Animals treated with GM-CSF alone exhibited a similar rate of tumor growth. Animals treated with saline and irradiated cells displayed a somewhat slower rate of growth reaching a mean volume of approximately 30,000 mm$^3$ by 52 days after implantation.

In contrast to these three groups of animals, those treated with both GM-CSF and irradiated tumor cells exhibited a complete regression of tumors. These results demonstrate that both GM-CSF and irradiated tumor cells are required for the regression of the intraflank tumor, and that the combination of these two therapies results in a synergistic effect that is not seen with either agent alone.

To verify that this anti-tumor response was immune-mediated rather than simply toxic to the growing tumor, the animals previously "cured" of their tumors were re-challenged with peripheral injections of 9L glioblastoma cells. Seventy (70) days had elapsed without treatment prior to rechallenge with tumor cells. Naive controls all developed tumors within 14 days. In contrast, all animals previously treated with GM-CSF and irradiated tumor cells were resistant to subsequent challenges with glioblastoma.

EXAMPLE 3

Effects of GM-CSF on Intracerebral Brain Tumors

To determine the efficacy of peripherally co-administered GM-CSF and tumor antigen on the survival of rats with intracerebral brain tumors, 9L tumors were established in the brains of host animals. Fischer 344 female rats (150–200 g) received intracerebral injections of one million 9L cells in PBS by stereotaxic injection into the striatum. On the same day, Alza pumps were implanted subcutaneously in each animal's flank, set to release GMCSF at a rate of 10 ng/day. Following the methods described for Example 1, irradiated 9L cells were injected into the site of GM-CSF release at the time of intracerebral tumor implantation (day 0) as well as at 3 and 7 days post implantation. Control animals had established intracerebral tumors, but received no peripheral therapy.

Figure 4:
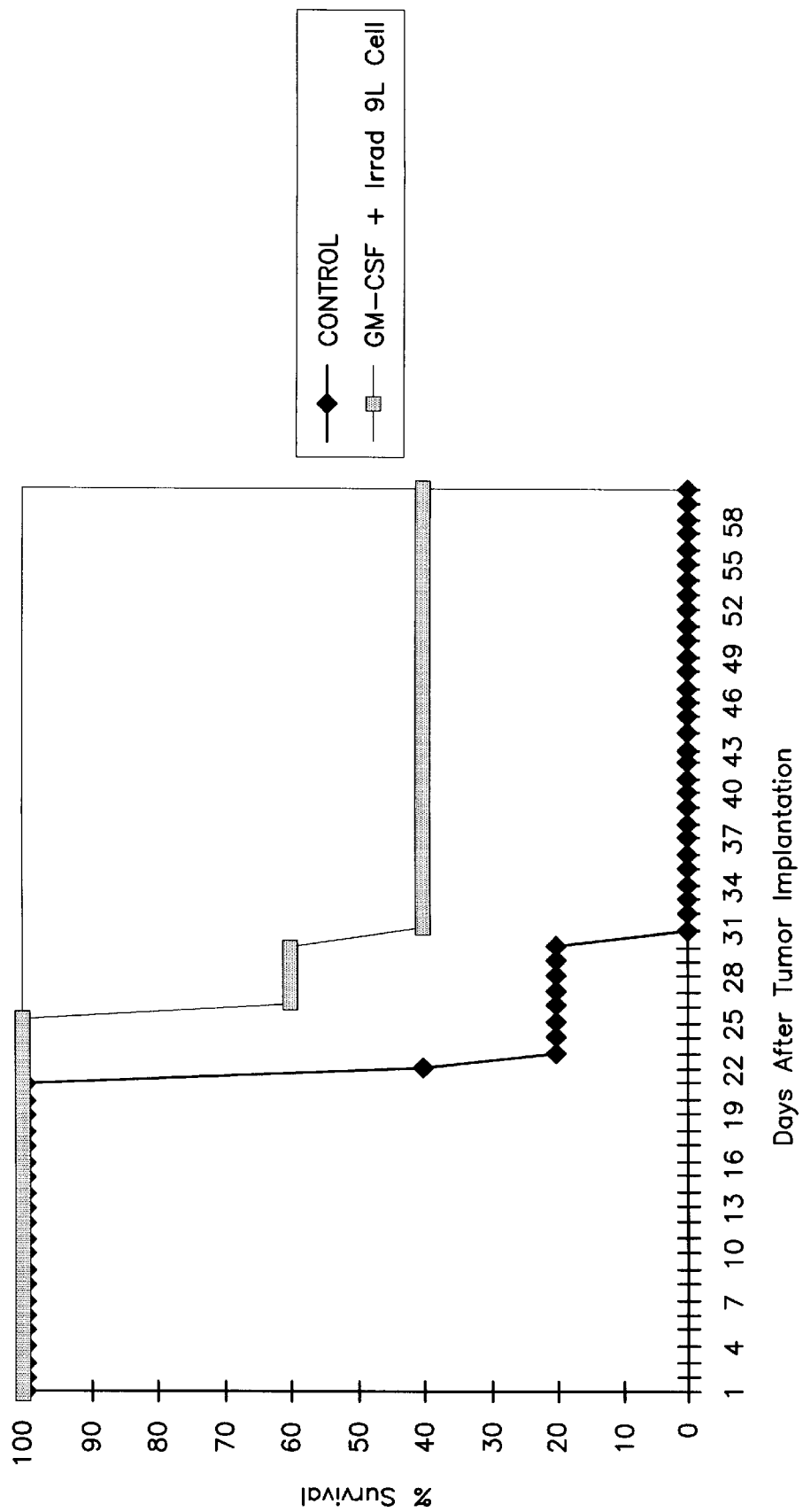
FIG. 4 is a graph showing the effect of peripheral co-administration of GM-CSF and tumor antigen on the growth of intracerebral 9L glioblastoma tumors.

As shown in FIG. 4, approximately 22 days after implanting the 9L tumors, most of the control animals had succumbed to the brain tumors. All of the animals in this group had died by day 31. In contrast, 40% of the animals receiving the GM-CSF/irradiated cell vaccinations survived beyond 167 days and have yet to expire. Localized subcutaneous delivery of GM-CSF in combination with delivery of tumor antigen (irradiated tumor cells) initiated a systemic response which led to the regression of distal intracerebral tumors.

The rodent model has been used to study immunotherapeutic approaches for the treatment of other types of cancer, e.g. melanomas and lymphomas, in immunocompetent mice or rats. Clinical trials now indicate that the rodent model for immunotherapy is very predictive of what is observed in humans.

The rat model provides an immune system similar to that of humans. The Fischer rat system also provides well-established syngeneic brain tumor lines that share identical immunological cell markers with the rat's normal cells, mimicking the case of human neoplasms.

It is therefore anticipated that the above-described studies using a rodent model for GM-CSF/irradiated tumor antigen treatment of brain tumors is predictive of the outcome of such treatment of human brain tumors.

What is claimed is:

1. A method for inhibiting the growth of brain tumor cells in a patient having a brain tumor, the method comprising:
   co-administering to the patient granulocyte/macrophage colony stimulating factor (GM-CSF) and brain tumor antigen obtained from said brain tumor.

2. A method for inhibiting recurrence of brain tumors in a patient, after brain tumor ablation, the method comprising:
   co-administering to the patient granulocyte/macrophage colony stimulating factor and brain tumor antigen obtained from said tumor.

3. The method of claim 1, wherein said brain tumor antigen comprises inactivated brain tumor cells or brain tumor cell lysate.

4. The method of claim 3, wherein said brain tumor antigen comprises irradiated brain tumor cells.

5. The method of claim 1, wherein said co-administering is to a peripheral, non central nervous system site.

6. The method of claim 5, wherein said co-administering of granulocyte/macrophage colony stimulating factor and brain tumor antigen is essentially simultaneous.

7. The method of claim 6, wherein said granulocyte/macrophage colony stimulating factor is administered by continuous infusion.

8. The method of claim 7, wherein said brain tumor antigen is administered by at least one injection.

9. The method of claim 7, wherein said granulocyte/macrophage colony stimulating factor and brain tumor antigen are co-administered for a time sufficient to induce an immnune response against the brain tumor.

10. A method for treating a patient suffering from brain cancer, the method comprising co-administering to the patient at a peripheral, non-central nervous system site, gianulocyte/macrophage colony stimulating factor and brain tumor antigen obtained from said brain cancer.

11. The method of claim 10, wherein the brain cancer is glioblastoma.

* * * * *